US011561884B2

(12) United States Patent
Shah

(10) Patent No.: US 11,561,884 B2
(45) Date of Patent: Jan. 24, 2023

(54) COMPUTER-CONTROLLED METRICS AND TASK LISTS MANAGEMENT

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 126 days.

(21) Appl. No.: 16/952,063

(22) Filed: Nov. 18, 2020

(65) Prior Publication Data
US 2021/0073105 A1    Mar. 11, 2021

(51) Int. Cl.
*G06F 11/00* (2006.01)
*G06F 11/36* (2006.01)
*G06F 11/22* (2006.01)

(52) U.S. Cl.
CPC ........ *G06F 11/366* (2013.01); *G06F 11/2263* (2013.01)

(58) Field of Classification Search
CPC .. G06F 11/0793; G06F 11/079; G06F 11/366; G06F 11/2263; G06N 20/00
See application file for complete search history.

(56) References Cited

U.S. PATENT DOCUMENTS

| 6,666,049 B1 | 12/2003 | Katende et al. |
| 6,907,416 B2 | 6/2005 | Tasooji et al. |
| 2006/0161800 A1 * | 7/2006 | Dathathraya ......... G06F 11/366 714/4.1 |
| 2006/0235280 A1 | 10/2006 | Vonk et al. |
| 2013/0218588 A1 | 8/2013 | Kehr et al. |
| 2015/0112710 A1 | 4/2015 | Haber et al. |
| 2015/0134265 A1 | 5/2015 | Kohlbrecher et al. |
| 2018/0210808 A1 * | 7/2018 | Shanmugam ......... G06F 11/366 |
| 2020/0065218 A1 * | 2/2020 | Bhosale ................ G06F 11/366 |
| 2022/0114041 A1 * | 4/2022 | Tiwari .................. H04L 41/065 |

FOREIGN PATENT DOCUMENTS

CA    2696082 C    2/2009

\* cited by examiner

*Primary Examiner* — Jonathan D Gibson
(74) *Attorney, Agent, or Firm* — Rahman LLC

(57) ABSTRACT

An electronic evaluation device and method thereof for optimizing an operation of computer-controlled metric appliances in a network. The method includes determining whether a fault associated with computer-controlled metric appliance is valid based on a feedback received in real time from a validation entity and updating pre-defined programmable instructions assigned to the computer-controlled metric appliance in response to determining that the fault is invalid. The predefined programmable instructions are used to determine whether the computer-executable metric is achieved or not. The method includes applying a machine learning model on the plurality of parameters and the computer-executable goal to determine a computer-executable task list to be assigned to the computer-controlled metric appliance in order to achieve the computer-executable goal.

24 Claims, 7 Drawing Sheets

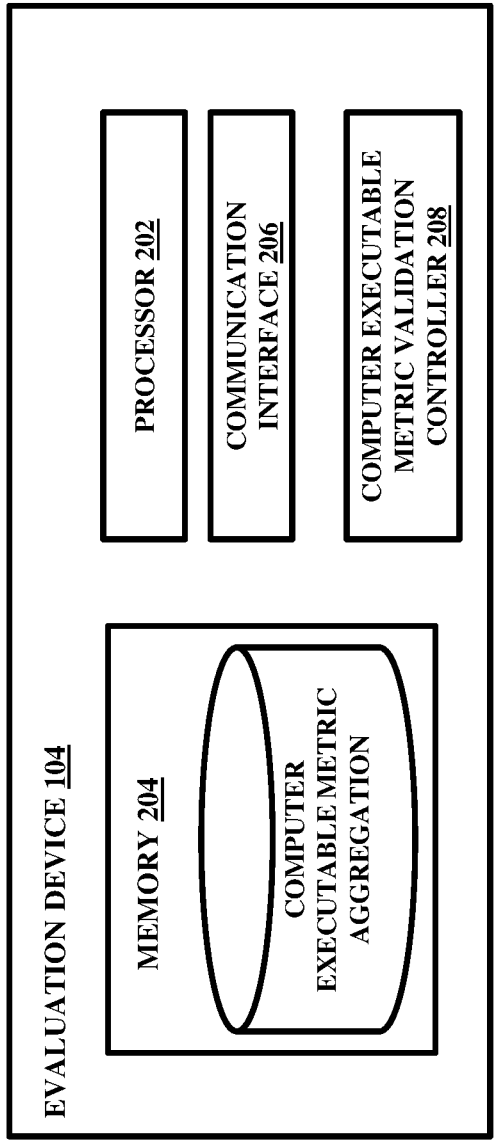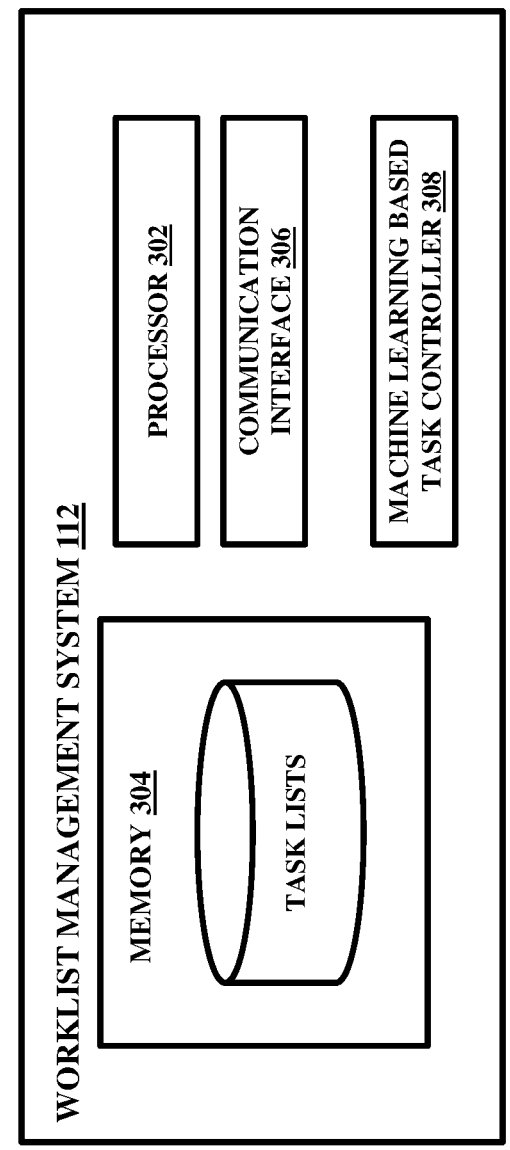

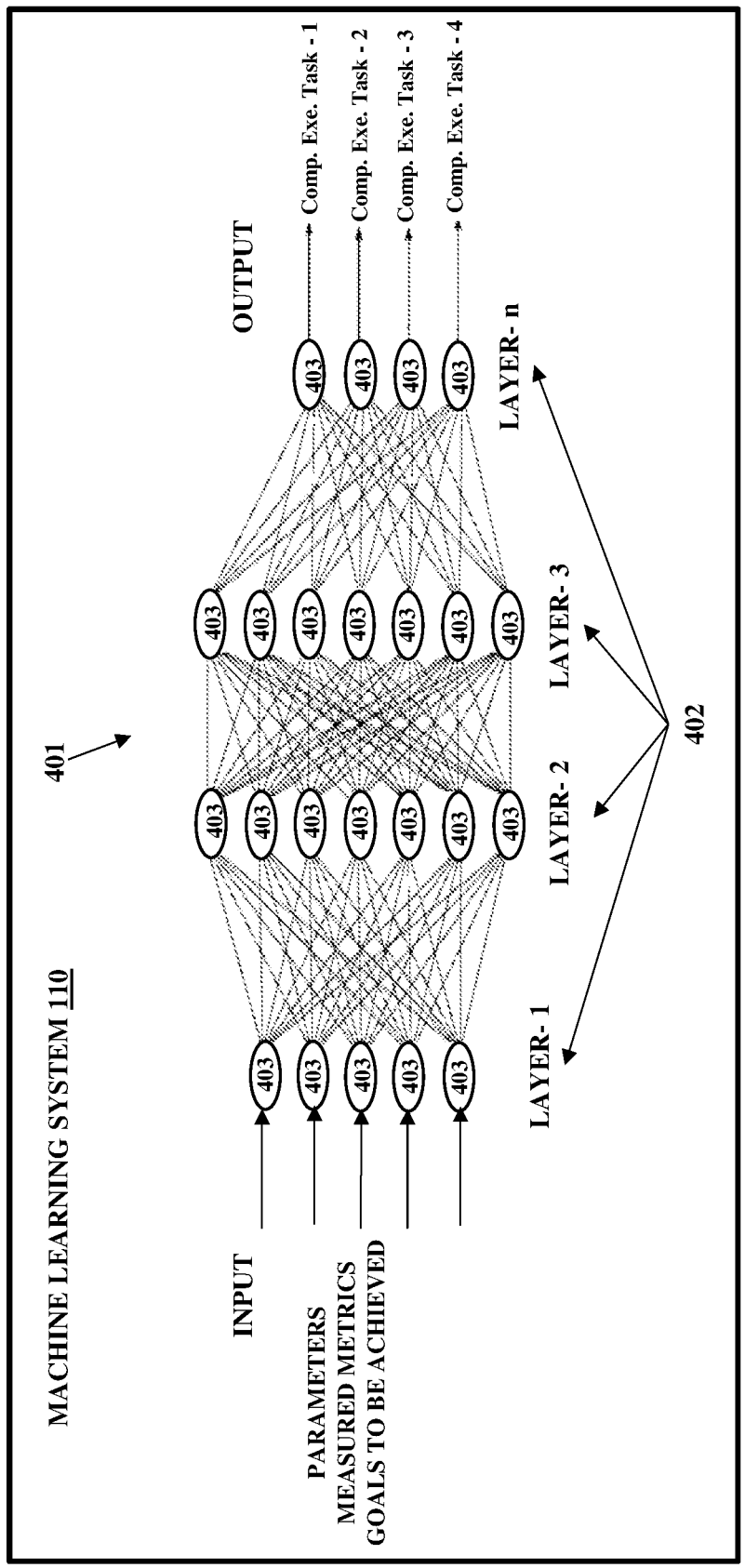

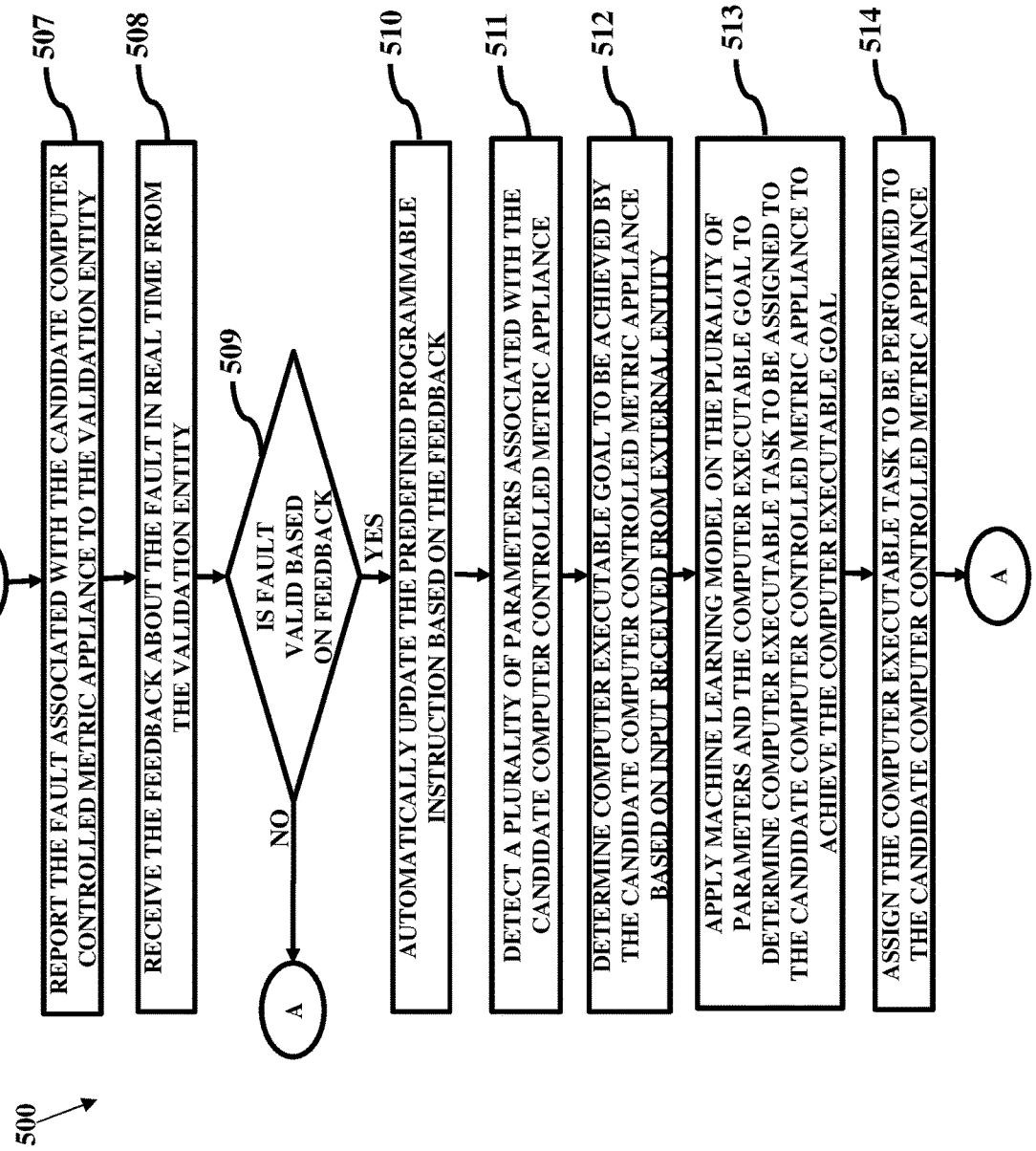

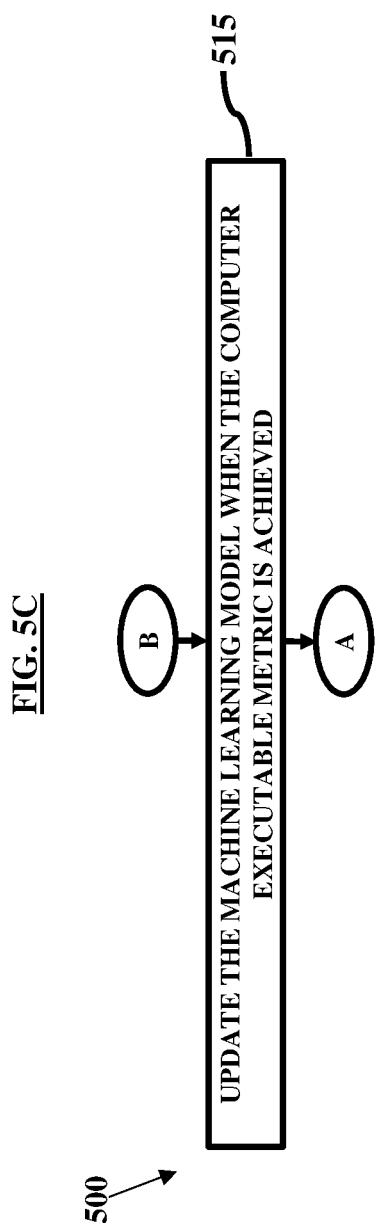

COMPUTER-CONTROLLED METRICS AND TASK LISTS MANAGEMENT

BACKGROUND

Technical Field

The embodiments herein relate to networked systems and, more particularly to a device and method for optimizing operation of networked and computer-controlled appliances generating certain metrics.

Description of the Related Art

Conventionally, automated devices perform operations based on predefined programmable instructions assigned for them. These instructions allow some tasks to be performed irrespective of whether an outcome achieved is desired or not. The instructions take care of performance metrics but not the desired outcome expected from these devices. In many cases, these devices may have to be operated manually or differently based on real-time situations which may cause actual performance metrics to deviate from predefined metrics defined for them. Accordingly, there is a need of a system that is capable of optimizing performance of devices in a network based on contextual situations in which they have to operate.

SUMMARY

In view of the foregoing, an embodiment herein provides a computer-implemented method for optimizing an operation of computer-controlled metric appliances in a network. The method includes receiving a computer-executable metric recorded by a computer-controlled metric appliance from the computer-controlled metric appliances, and detecting a fault associated with the computer-controlled metric appliance based on predefined programmable instructions provided to the computer-controlled metric appliance. The predefined programmable instructions are used to determine whether the computer-executable metric is achieved or not. The method includes receiving, by the electronic evaluation device, a feedback about the fault in real time from a validation entity in response to detecting the fault, determining, by the electronic evaluation device, whether the fault associated with the computer-controlled metric appliance is valid based on the feedback received in real time from the validation entity, and automatically updating the predefined programmable instructions provided to the computer-controlled metric appliance based on the feedback in response to determining that the fault is invalid. The predefined programmable instructions, after updating, changes an expected outcome of the computer-executable metric resulting in an optimized performance of the computer-controlled metric appliance.

In an embodiment, detecting, by the electronic evaluation device, the fault associated with the computer-controlled metric appliance may include determining whether the computer-executable metric is achieved or not by comparing the computer-executable metric recorded by the computer-controlled metric appliance with the predefined programmable instructions provided to the computer-controlled metric appliance, detecting, by the electronic evaluation device, that the computer-executable metric is not achieved in response to determining that the computer-executable metric recorded by the computer-controlled metric appliance does not match with the pre-defined programmable instructions provided to the computer-controlled metric appliance, and detecting the fault associated with the computer-controlled metric appliance in response to determining that the computer-executable metric is not achieved.

In an embodiment, receiving, by the electronic evaluation device, the feedback about the fault may include determining whether the fault associated with the computer-controlled metric appliance meets a fault threshold in response to detecting the fault, reporting the fault associated with the computer-controlled metric appliance to the validation entity in response to determining that the fault associated with the computer-controlled metric appliance meets the fault threshold, and receiving the feedback about the fault in real time from the validation entity.

The method may further include detecting a plurality of parameters associated with the candidate computer-controlled metric appliance, determining a computer-executable goal to be achieved by the computer-controlled metric appliance, applying a machine learning model on the plurality of parameters and the computer-executable goal to determine a computer-executable task to be assigned to the computer-controlled metric appliance to achieve the computer-executable goal, and assigning the computer-executable task to the computer-controlled metric appliance.

In an embodiment, determining the computer-executable goal to be achieved may include receiving an input from an external entity, and determining the computer-executable goal to be achieved by the computer-controlled metric appliance based on the input.

The method may include receiving the computer-executable metric recorded by the computer-controlled metric appliance and determining whether the computer-executable metric is achieved or not by comparing the computer-executable metric recorded by the computer-controlled metric appliance with the pre-defined programmable instructions provided to the computer-controlled metric appliance. In response to determining that the computer-executable metric recorded by the computer-controlled metric appliance does not match with the predefined programmable instructions provided to the computer-controlled metric appliance, detecting that the computer-executable metric is not achieved, detecting the fault associated with the computer-controlled metric appliance in response to determining that the computer-executable metric is not achieved, and correcting the machine learning model to optimize determination of the computer-executable task assigned to the computer-controlled metric appliance. In response to determining that the computer-executable metric recorded by the computer-controlled metric appliance matches with the pre-defined programmable instructions provided to the computer-controlled metric appliance, detecting that the computer-executable metric is achieved, and updating the machine learning model in response to detecting that the computer-executable metric is achieved.

The method may include generating an output signal by the electronic evaluation device, wherein the output signal triggers a change in operation of the computer-controlled metric appliance if the fault is identified to be valid. The change in operation of the computer-controlled metric appliance may signify executing one or more tasks by the computer-controlled metric appliance based on an updated set of the predefined programmable instructions.

The plurality of parameters may include a location of the computer-controlled metric appliance, a type of the computer-controlled metric appliance, a capability of the computer-controlled metric appliance, a user associated with the computer-controlled metric appliance, and historic values of the computer-executable metric generated by the computer-controlled metric appliance.

Another embodiment herein provides a computer-implemented method for optimizing an operation of computer-controlled metric appliances in a network. The method includes detecting a plurality of parameters associated with a candidate computer-controlled metric appliance from the computer-controlled metric appliances, determining a computer-executable goal to be achieved by the candidate computer-controlled metric appliance, determining a computer-executable task list to be assigned to the candidate computer-controlled metric appliance to achieve the computer-executable goal based on the plurality of parameters and the computer-executable goal by applying a machine learning model, and assigning the computer-executable task list to the candidate computer-controlled metric appliance. The assigning of the computer-executable task list to the candidate computer-controlled metric appliance facilitates achieving the computer-executable goal by the candidate computer-controlled metric appliance.

In an embodiment, determining the computer-executable goal to be achieved may include receiving an input from an external entity, and determining the computer-executable goal to be achieved by the candidate computer-controlled metric appliance based on the input.

The method may include receiving a feedback about the fault in real time from a validation entity in response to detecting the fault, determining whether the fault associated with the candidate computer-controlled metric appliance is valid based on the feedback received in real time from the validation entity, and automatically updating a predefined programmable instructions based on the feedback in response to determining that the fault is invalid.

In an embodiment, receiving the feedback about the fault in real time may include determining whether the fault associated with the candidate computer-controlled metric appliance meets a fault threshold in response to detecting the fault, reporting the fault associated with the candidate computer-controlled metric appliance to the validation entity in response to determining that the fault associated with the candidate computer-controlled metric appliance meets the fault threshold, and receiving the feedback about the fault in real time from the validation entity.

Another embodiment herein provides an electronic evaluation device for optimizing an operation of computer-controlled metric appliances in a network. The electronic evaluation device includes a memory, a processor, and a computer-executable metric validation controller communicatively coupled to the memory and the processor. The executable metric validation controller is configured to receive a computer-executable metric recorded by a candidate computer-controlled metric appliance from the computer-controlled metric appliances, and detect a fault associated with the candidate computer-controlled metric appliance based on predefined programmable instructions provided to the candidate computer-controlled metric appliance. The pre-defined programmable instructions are used to determine whether the computer-executable metric is achieved or not. The metric validation controller is configured to receive a feedback about the fault in real time from a validation entity in response to detecting the fault, determine whether the fault associated with the candidate computer-controlled metric appliance is valid based on the feedback received in real time from the validation entity, and automatically update the predefined programmable instructions based on the feedback in response to determining that the fault is invalid. An updating of the predefined programmable instructions allows the candidate computer-controlled metric appliance to achieve the computer-executable metric.

The electronic evaluation device may be further configured to determine whether the computer-executable metric is achieved or not by comparing the computer-executable metric recorded by the candidate computer-controlled metric appliance with the predefined programmable instructions provided to the candidate computer-controlled metric appliance. In response to determining that the computer-executable metric recorded by the candidate computer-controlled metric appliance does not match the predefined programmable instructions assigned to the candidate computer-controlled metric appliance, detect that the computer-executable metric is not achieved. In response to determining that the computer-executable metric is not achieve, detect the fault associated with the candidate computer-controlled metric appliance in response to determining that the computer-executable metric is not achieved.

The electronic evaluation device may be further configured to determine whether the fault associated with the candidate computer-controlled metric appliance meets a fault threshold in response to detecting the fault, report the fault associated with the candidate computer-controlled metric appliance to the validation entity in response to determining that the fault associated with the candidate computer-controlled metric appliance meets the fault threshold, and receive the feedback about the fault in real time from the validation entity.

In an embodiment, the electronic evaluation device may include a machine learning based task controller configured to detect a plurality of parameters associated with the candidate computer-controlled metric appliance, determine a computer-executable goal to be achieved by the candidate computer-controlled metric appliance, apply a machine learning model on the plurality of parameters and the computer-executable goal to determine a computer-executable task to be assigned to the candidate computer-controlled metric appliance to achieve the computer-executable goal, and assign the computer-executable task to the candidate computer-controlled metric appliance.

The electronic evaluation device may be further configured to receive an input from an external entity, and determine the computer-executable goal to be achieved by the candidate computer-controlled metric appliance based on the input.

The machine learning based task controller may be further configured to receive a computer-executable metric recorded by a candidate computer-controlled metric appliance, and determine whether the computer-executable metric is achieved or not by comparing the computer-executable metric recorded by the candidate computer-controlled metric appliance with the predefined programmable instructions provided to the candidate computer-controlled metric appliance. In response to determining that the computer-executable metric recorded by the candidate computer-controlled metric appliance does not match with the predefined programmable instructions assigned to the candidate computer-controlled metric appliance, the machine learning based task controller may be further configured to detect that the computer-executable metric is not achieved, detect the fault associated with the candidate computer-controlled metric appliance in response to determining that the computer-executable metric is not achieved, and correct the machine learning model to optimize determination of the computer-executable task to be assigned to the candidate computer-controlled metric appliance. Further, in response to determining that the computer-executable metric recorded by the candidate computer-controlled metric appliance matches with the pre-defined programmable instructions assigned to the candidate computer-controlled metric appliance, the machine learning based task controller may be further configured to detect that the computer-executable metric is achieved, and update the machine learning model in response detecting that the computer-executable metric is achieved.

Another embodiment herein provides an electronic evaluation device for optimizing an operation of computer-controlled metric appliances in a network. The electronic evaluation device includes a memory, a processor and a computer-executable metric validation controller communicatively coupled to the memory and the processor. The executable metric validation controller is configured to detect a plurality of parameters associated with a candidate computer-controlled metric appliance from the computer-controlled metric appliances, determine a computer-executable goal to be achieved by the candidate computer-controlled metric appliance, determine a computer-executable task list to be assigned to the candidate computer-controlled metric appliance to achieve the computer-executable goal based on the plurality of parameters and the computer-executable goal by applying a machine learning model, and assign the computer-executable task list to the candidate computer-controlled metric appliance. An assigning of the computer-executable task list to the candidate computer-controlled metric appliance facilitates achieving the computer-executable goal by the candidate computer-controlled metric appliance.

The electronic evaluation device may be further configured to receive an input from an external entity and determine the computer-executable goal to be achieved by the candidate computer-controlled metric appliance based on the input.

The machine learning based task controller may be configured to receive a feedback about the fault in real time from a validation entity in response to detecting the fault, determine whether the fault associated with the candidate computer-controlled metric appliance is valid based on the feedback received in real time from the validation entity, and automatically update predefined programmable instructions based on the feedback in response to determining that the fault is invalid.

In an embodiment, receiving the feedback about the fault in real time includes determining whether the fault associated with the candidate computer-controlled metric appliance meets a fault threshold in response to detecting the fault, reporting the fault associated with the candidate computer-controlled metric appliance to the validation entity in response to determining that the fault associated with the candidate computer-controlled metric appliance meets the fault threshold, and receiving the feedback about the fault in real time from the validation entity.

Another embodiment herein provides a computer-implemented method for optimizing an operation of computer-controlled metric appliances in a network. The method includes receiving, by an electronic evaluation device, a computer-executable metric recorded by a computer-controlled metric appliance from among the computer-controlled metric appliances, wherein the computer-executable metric is generated based on a predefined programmable instructions for the computer-controlled metric appliance. The method includes detecting, by the electronic evaluation device, a set of data inputs requiring a refinement in the predefined programmable instructions provided to the computer-controlled metric appliance, wherein the predefined programmable instructions are used to determine whether the computer-executable metric is achieved or not based on assigned computer-executable tasks. The method includes automatically updating, by the electronic evaluation device, the predefined programmable instructions provided to the computer-controlled metric appliance such that the predefined programmable instructions after updating changes an expected outcome of the computer-executable metric resulting in an optimized performance of the computer-controlled metric appliance.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 2 illustrates a block diagram of an electronic evaluation device, according to embodiments as disclosed herein;

FIG. 3 illustrates a block diagram of a worklist management system, according to embodiments as disclosed herein;

FIG. 4 illustrates working of a machine learning system, according to embodiments as disclosed herein;

FIGS. 5A-5C illustrate a method for optimizing an operation of computer-controlled metric appliances.

DETAILED DESCRIPTION

Figure 1:
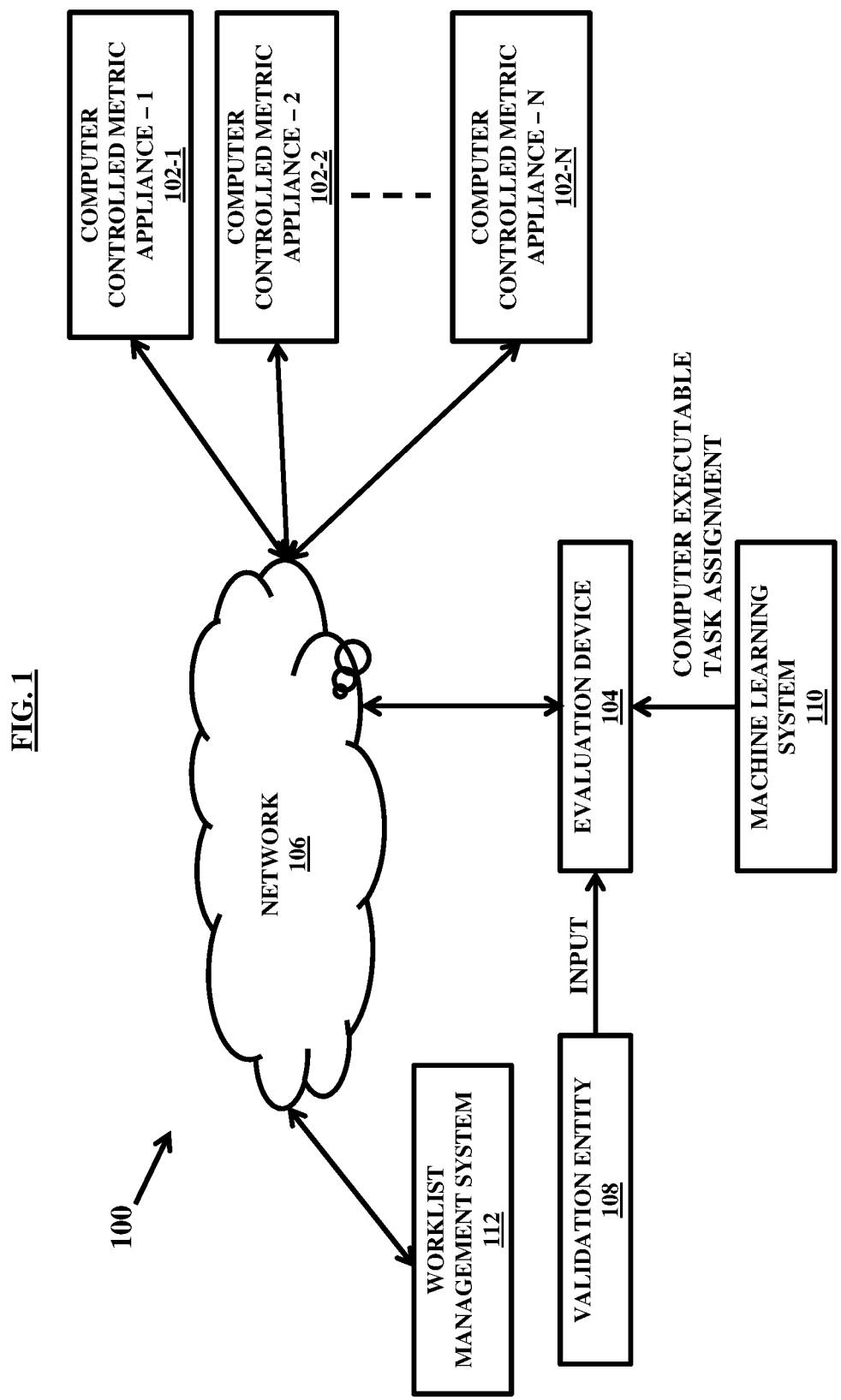
FIG. 1 illustrates a high-level overview of a system, according to embodiments as disclosed herein.

The embodiments herein and the various features and advantageous details thereof are explained more fully with reference to the non-limiting embodiments that are illustrated in the accompanying drawings and detailed in the following description. Descriptions of well-known components are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein may be described and illustrated in terms of blocks which carry out a described function or functions. These blocks, which may be referred to herein as units or modules or the like, are physically implemented by analog or digital circuits such as logic gates, integrated circuits, microprocessors, microcontrollers, memory circuits, passive electronic components, active electronic components, optical components, hardwired circuits, or the like, and may optionally be driven by firmware and software. The circuits may, for example, be embodied in one or more semiconductor chips, or on substrate supports such as printed circuit boards and the like. The circuits constituting a block may be implemented by dedicated hardware, or by a processor (e.g., one or more programmed microprocessors and associated circuitry), or by a combination of dedicated hardware to perform some functions of the block and a processor to perform other functions of the block. Each block of the embodiments may be physically separated into two or more interacting and discrete blocks without departing from the scope of the invention. Likewise, the blocks of the embodiments may be physically combined into more complex blocks without departing from the scope of the invention The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings. Although the terms first, second, etc. may be used herein to describe various elements, these elements should not be limited by these terms. These terms are generally only used to distinguish one element from another.

Referring now to the drawings, and more particularly to FIGS. 1-6, there are shown exemplary embodiments.

FIG. 1 illustrates a high-level overview of a system 100, according to embodiments as disclosed herein. The system 100 includes computer-controlled metric appliances 102-1 . . . 102-N connected to an electronic evaluation device 104 using a network 106 for facilitating transmission of signals containing at least metrics associated with the computer-controlled metric appliances 102-1 . . . 102-N, a validation entity 108 to provide feedback to the electronic evaluation device 104, and a machine learning system 110 to generate and train a machine learning model that learns behavior of the computer-controlled metric appliances 102-1 . . . 102-N, fault detection pattern, and suitable computer-executable task lists for each of the computer-controlled metric appliances 102-1 . . . 102-N. The system 100 includes a worklist management system 112 to monitor performance of the computer-controlled metric appliances 102-1 . . . 102-N and assign a goal-based computer-executable task list also referred to as worklist to one or more of the computer-controlled metric appliances 102-1 . . . 102-N in accordance with a set of predefined computer-executable goals.

Each of the computer-controlled metric appliances 102-1 . . . 102-N includes a memory that stores predefined programmable instructions and one or more processors configured to execute the predefined programmable instructions and record one or more computer-executable metric. The one or more computer-executable metric (referred to herein as computer-executable metric or metric) includes a signal indicative of performance of a computer-controlled metric appliance such as 102-1 and collected from a set of operations performed by the computer-controlled metric appliance 102-1. The metric may be collected from the computer-controlled metric appliances 102-1 to monitor and evaluate performance measures digitally over the network 106.

A computer-controlled metric appliance 102-1 . . . 102-N—may include, but is not limited to, a cellular phone, a smart phone, a Personal Digital Assistant (PDA), a tablet computer, a laptop computer, an Internet of Things (IoT) device, a virtual reality device, a flexible electronic device, a curved electronic device, and a foldable electronic device. The types of computer-controlled metric appliances 102-1 . . . 102-N used in a scenario may depend on an application in which the invention is practiced. For example, in a healthcare domain, non-limiting examples of the computer-controlled metric appliances 102-1 . . . 102-N can include blood pressure (BP) monitoring devices, electroencephalography (EEG) devices, glucose monitoring devices, drug delivery devices, atrial fibrillation (AF) devices, and other medical devices. In a networking domain, non-limiting examples of the computer-controlled metric appliances 102-1 . . . 102-N may include routers, switches, beacons, sensors, and wireless computers. In an aerospace domain, non-limiting examples of the computer-controlled metric appliances 102-1 . . . 102-N may include aircraft electrical system, aircraft safety system, electrical engines, battery systems, wireless sensors, ventilation systems, and other aircraft devices.

In an example, the computer-controlled metric appliances 102-1 . . . 102-N may refer to an "instrument" which may include without limitations medical device instruments, survey instruments, standalone wearables, and a variety of other "instruments" that may or may not be computer-controlled.

In an example, the network 106 may include, but is not limited to, a wireless network, an Internet of Thing (IoT) network, a wired network, or a trusted network such as a block chain network and a combination thereof.

Each of the computer-controlled metric appliances 102-1 . . . 102-N may record the computer-executable metric and send the computer-executable metric to the electronic evaluation device 104 via the network 106. In an embodiment, the computer-controlled metric appliance 102-1 . . . 102-N sends the computer-executable metric continuously or on a predefined interval as configured by the electronic evaluation device 104.

Non-limiting examples of the electronic evaluation device 104 includes but are not limited to a cloud server, a central server, an individual computer, and a central controller in an IoT network. The electronic evaluation device 104 may be configured to receive the computer-executable metric recorded by the computer-controlled metric appliances 102-1 . . . 102-N and detect a fault or a gap or an error associated with the computer-controlled metric appliances 102-1 . . . 102-N based on predefined programmable instructions assigned to the computer-controlled metric appliances 102-1 . . . 102-N. The predefined programmable instructions are used to determine whether the computer-executable metric is achieved or not. Upon detection of the fault or the gap, the electronic evaluation device 104 elicits a feedback from the validation entity 108 to validate the fault. Upon detection that the fault as invalid, the electronic evaluation device 104 automatically updates the predefined programmable instructions based on the feedback.

In an example, the term fault may be defined as a gap or a difference or an error in the actual value of metric as compared to a value defined for an appliance to perform based on the predefined programmable instructions.

In an example, the fault may be defined as a possible refinement needed in the metric in view of certain expected outcomes even if there is no error detected. In such a scenario, the electronic evaluation device 104 may update the predefined programmable instructions based on a feedback from a human-attestation or in an automated manner by a machine in view of real-world data inputs.

In an embodiment, the refinements may be tied to the expected outcomes as identified by the electronic evaluation device 104 using artificial intelligence/machine learning (AI/ML) algorithms and systems. For example, the AI/ML algorithms may detect new inputs and patterns associated with the tasks executed by the computer-controlled metric appliances 102-1 . . . 102-N which may not necessarily be indicative of the errors but new data that require new rules, decisions, and logics for performance and metrics evaluation. The electronic evaluation device 104 may accordingly make the necessary refinements so as to change values of expected metrics for subsequent performance and task execution.

In an example, a computer-implemented method for optimizing an operation of the computer-controlled metric appliances 102-1 . . . 102-N in the network 106 may include receiving, by the electronic evaluation device 104, a computer-executable metric recorded by a computer-controlled metric appliance 102-1 . . . 102-N, wherein the computer-executable metric is generated based on the predefined programmable instructions for the computer-controlled metric appliance 102-1 . . . 102-N. The method may include detecting, by the electronic evaluation device 104, the data inputs and patterns requiring the refinement in the pre-defined programmable instructions provided to the computer-controlled metric appliance 102-1 . . . 102-N, wherein the pre-defined programmable instructions are used to determine whether the computer-executable metric is achieved or not based on assigned computer-executable tasks. The method may include automatically updating, by the electronic evaluation device 104, the pre-defined programmable instructions provided to the computer-controlled metric appliance 102-1 . . . 102-N such that the predefined programmable instructions after updating changes an expected outcome of the computer-executable metric.

The electronic evaluation device 104 takes corrective actions (referred as "actionable reactions") based on the feedback received in view of the real-world inputs for possible refinements. In an embodiment, the electronic evaluation device 104 implements open policy agency (OPA) and related evaluation for metrics across multiple ecosystems (for example, checking one metric in a human-attestation against a real metric coming out of a hardware device to validate data and using the real-time feedback from the validation entity 108 will further improvise the overall evaluation process. The real-time feedback may indicate for corrective actions and refinements to be taken at the computer-controlled metric appliance 102-1 . . . 102-N.

Examples of the validation entity 108 include but are not limited to, a user of the electronic evaluation device 104, an administrator of a computer-controlled metric appliance such as the computer-controlled metric appliance 102-1 . . . 102-N, or any system which is communicatively connected to the computer-controlled metric appliance 102-1 . . . 102-N.

The electronic evaluation device 104 takes corrective actions (referred to as "actionable reactions") based on the feedback received from the validation entity 108. In an embodiment, the electronic evaluation device 104 implements open policy agency (OPA) and related evaluation for metrics across multiple technological implementations involving manual or machine-involved verification (for example, checking one metric in a human-attestation against a real metric coming out of a hardware device to validate data and using the real-time feedback from the validation entity 108 will further improvise the overall evaluation process). The real-time feedback from the validation entity 108 may indicate for corrective actions to be taken at the computer-controlled metric appliance 102-1 . . . 102-N which led the computer-controlled metric appliance 102-1 . . . 102-N to deviate from achieving the metric based on the predefined programmable instructions or which caused an incorrect interpretation for something that is otherwise found correct through human attestation because of exceptional or different scenarios that the metric appliance 102-1 . . . 102-N might have not been taught to recognize because of lack of machine learning. For example, a patient monitor reports that a patient's blood pressure or body temperature was reported as X but a nurse wrote down Y. The electronic evaluation device 104 may be configured to identify this kind of error or discrepancy based on the real-time feedback from the validation entity 108.

The worklist management system 112 may be configured to use as inputs a plurality of parameters associated with the computer-controlled metric appliance 102-1 . . . 102-N and apply one or more machine learning models on the plurality of parameters in order to determine a goal-based computer-executable task list based on a pre-defined set of computer-executable goals for the computer-controlled metric appliance 102-1 . . . 102-N. The computer-executable task list may be assigned to the computer-controlled metric appliance 102-1 . . . 102-N to perform its operation according to the predefined set of computer-executable goals.

In an exemplary scenario, there may be situations or devices who know their tasks but do not know when to perform them (either by schedule, location, etc.). There are a lot of tasks that are supposed to be performed at particular times over a particular period of time at a particular location. The worklist management system 112 may allow to establish a goal with a common set of tasks that have to be performed in specific order by specific people or devices in particular location by the computer-controlled metric appliance 102-1 . . . 102-N. The worklist management system 112 defines such goal-based task lists for each of the computer-controlled metric appliances 102-1 . . . 102-N based on the various parameters and trained machine learning models.

In an embodiment, the plurality of parameters includes, but are not limited to, a location of the computer-controlled metric appliance 102-1 . . . 102-N, a type of the computer-controlled metric appliance 102-1 . . . 102-N, a capability of the computer-controlled metric appliance 102-1 . . . 102-N, a user associated with the computer-controlled metric appliance 102-1 . . . 102-N, and historic values for the computer-executable metrics associated with the computer-controlled metric appliance 102-1 . . . 102-N.

The worklist management system 112 may provide these parameters as an input to the machine learning system 110 to determine the goal-based computer-executable task list to be assigned to the computer-controlled metric appliance 102-1 . . . 102-N to achieve the computer-executable goals.

The machine learning system 110 may include a pre-defined operating rule or artificial intelligence (AI) model that may be provided through training or learning. By applying a learning technique to the computer-executable metrics collected by the worklist management system 112, the predefined operating rule or AI model of a desired characteristic may be defined. The learning may be performed in the device itself according to an embodiment, and/or may be implemented through a separate server/system.

The AI model may comprise a plurality of neural network layers. Each layer may include a plurality of weight values and may perform a layer operation through calculation of a previous layer and an operation on a plurality of weights. Examples of neural networks may include, but are not limited to, convolutional neural network (CNN), deep neural network (DNN), recurrent neural network (RNN), restricted Boltzmann Machine (RBM), deep belief network (DBN), bidirectional recurrent deep neural network (BRDNN), generative adversarial networks (GAN), and deep Q-networks.

The electronic evaluation device 104 is further described in conjunction with FIG. 2. The worklist management system 112 is further discussed in conjunction with FIG. 3.

FIG. 2, with reference to FIG. 1, illustrates a block diagram of the electronic evaluation device 104, according to embodiments as disclosed herein. The electronic evaluation device 104 includes a processor 202, a memory 204, a communication interface 206, and a computer-executable metric validation controller 208.

The processor 202 may include, such as a central processing unit (CPU), an application processor (AP), or the like, a graphics-only processing unit such as a graphics processing unit (GPU), a visual processing unit (VPU) and the like. The processor 202 may include multiple cores and is configured to execute instructions stored in the memory 204 and to perform various pre-defined tasks as discussed herein. The communication interface 206 is configured for establishing communication between internal hardware components and with external devices via the network 106. The communication interface 206 includes an electronic circuit specific to a standard that enables the evaluation device 104 to communicate with the worklist management system 112 and/or the machine learning system 110.

The memory 204 stores the instructions that are executed by the processor 202. The memory 204 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. The memory 204, in some examples, may include a non-transitory storage medium. The term "non-transitory" may indicate that the storage medium is not embodied in a carrier wave or a propagated signal. However, the term "non-transitory" should not be interpreted that the memory 204 is non-movable. In certain examples, a non-transitory storage medium may store data that can, over time, change (e.g., in Random-access Memory (RAM) or cache).

The computer-executable metric validation controller 208 is implemented by processing circuitry such as logic gates, integrated circuits, microprocessors, microcontrollers, memory circuits, passive electronic components, active electronic components, optical components, hardwired circuits, or the like, and may optionally be driven by firmware and software. The circuits may, for example, be embodied in one or more semiconductor chips, or on substrate supports such as printed circuit boards and the like.

The computer-executable metric validation controller 208 may be configured to receive the computer-executable metric recorded by such as the computer-controlled metric appliance 102-1 . . . 102-N from the computer-controlled metric appliances 102-1 . . . 102-N and detect a fault associated with the computer-controlled metric appliance 102-1 . . . 102-N based on the predefined programmable instructions provided to the computer-controlled metric appliance 102-1 . . . 102-N and/or a worklist assigned to the computer-controlled metric appliance 102-1 . . . 102-N. The pre-defined programmable instructions may be used to determine whether the computer-executable metric is achieved or not by comparing the computer executable metric with an actual result or metric delivered by the computer-controlled metric appliance 102-1 . . . 102-N. In an embodiment, a decision about whether the computer-executable metric is achieved or not may be determined by comparing the computer-executable metric recorded by the computer-controlled metric appliance 102-1 . . . 102-N with the predefined programmable instructions assigned to the computer-controlled metric appliance 102-1 . . . 102-N.

If the computer-executable metric recorded by the computer-controlled metric appliance 102-1 . . . 102-N does not match with the predefined programmable instructions provided to the computer-controlled metric appliance 102-1 . . . 102-N, the computer-executable metric is considered as not achieved. If a match is found by comparing the computer executable metric, then the computer-executable metric is considered to be achieved. Further, when the computer-executable metric is not achieved, the fault or discrepancy associated with performance of the computer-controlled metric appliance 102-1 . . . 102-N may be identified and detected and evaluated through various means including human attestation to determine whether it was a real fault or not and accordingly use machine learning techniques to teach a machine for future cases involving similar scenarios when identifying faults.

For example, the predefined programmable instructions for a device such as an auto drug delivery appliance may be configured to deliver a predefined amount of a specific drug to a patient suffering with pneumonia. An attendant however may reconfigure the predefined programmable instructions or stop execution of the pre-defined programmable instructions for a period of time to not deliver the drug as per the predefined programmable instructions but change it to some other value in view of certain contextual parameters noted by the attendant after a due approval process. The computer-executable metric validation controller 208 may obtain the metric recorded by the auto drug delivery appliance and decide that the computer-executable metric is not achieved by the auto drug delivery appliance and declare a fault with the auto drug delivery appliance as the computer-executable metric recorded by the auto drug delivery appliance does not match with the predefined programmable instructions.

The computer-executable metric validation controller 208 may also determine if the fault or discrepancy associated with the computer-controlled metric appliance 102-1 . . . 102-N crosses a fault threshold or is within a permissible range. In response to detecting the fault crossing the threshold range or threshold count (such as when the fault repeats multiple times frequently), the validation controller 208 may report the fault associated with the computer-controlled metric appliance 102-1 . . . 102-N to the validation entity 108 and receive a feedback about the fault in real time from the validation entity 108.

For example, when a hospital administrator observes many similar medical device failures, the failure may be reported to an in charge handling the medical device to get a real time feedback related to the failures in order to validate the failures. In another example, when an aviation administrator observes that many failures were occurring in a jet, a message is sent to the technician/flight in charge to get the feedback in order to validate the failures and also determine whether they are real failures or something else. This may require a second layer of attestation such as human attestation or something else without limitations for verification of the faults associated with various collected metrics.

Further, the computer-executable metric validation controller 208 may determine whether the fault associated with the computer-controlled metric appliance 102-1 . . . 102-N is valid or invalid based on the feedback received in real time from the validation entity 108, and automatically update the predefined programmable instructions based on the feedback in response to determining that the fault is invalid.

Although the FIG. 2 shows various hardware components of the electronic evaluation device 104, it is to be understood that other embodiments are not limited thereon. Further, labels or names of the components as used herein are only for illustrative purposes and do not limit the scope of the invention. One or more components can be combined together to perform same or substantially similar function.

FIG. 3, with reference to FIGS. 1 and 2, illustrates a block diagram of the worklist management system 112, according to embodiments as disclosed herein. Examples of the worklist management system 112 include, but are not limited to, a cloud server, a central server, an individual computer, and a central controller in an IoT network designed and deployed for special purpose to perform a set of worklist management tasks as discussed elsewhere in the document. The worklist management system 112 includes a processor 302, a memory 304, a communication interface 306, and a machine learning based task controller 308.

The processor 302 may comprise a central processing unit (CPU), an application processor (AP), or the like, a graphics-only processing unit such as a graphics processing unit (GPU), a visual processing unit (VPU) and the like. The processor 302 may include multiple cores to execute instructions stored in the memory 304. The communication interface 306 is configured for communicating internally among internal hardware components and with external devices via the network 106.

The communication interface 306 may include an electronic circuit specific to a standard that enables the worklist management system 112 to communicate with the evaluation device 104 and/or machine learning system 110.

The memory 304 stores task lists for the computer-controlled metric appliance 102-1 . . . 102-N and the instructions to be executed by the processor 302 for assigning and executing the tasks lists (also referred to as worklists without limitations interchangeably) to the computer-controlled metric appliance 102-1 . . . 102-N as per requirements such as including assigning of the tasks lists in view of the goals as discussed elsewhere in the document without limitations. The memory 304 may include non-volatile storage elements. Examples of such non-volatile storage elements may include magnetic hard discs, optical discs, floppy discs, flash memories, or forms of electrically programmable memories (EPROM) or electrically erasable and programmable (EEPROM) memories. The memory 204 may, in some examples, include a non-transitory storage medium. The term "non-transitory" may indicate that the storage medium is not embodied in a carrier wave or a propagated signal. However, the term "non-transitory" should not be interpreted that the memory 304 is non-movable. In certain examples, a non-transitory storage medium may store data that can, over time, change (e.g., in Random-access Memory (RAM) or cache).

The machine learning based task controller 308 is implemented by a processing circuitry including such as logic gates, integrated circuits, microprocessors, microcontrollers, memory circuits, passive electronic components, active electronic components, optical components, hardwired circuits, or the like, and may optionally be driven by firmware and software. The processing circuitry may, for example, be embodied in one or more semiconductor chips, or on substrate supports such as printed circuit boards and the like.

The machine learning based task controller 308 may be configured to detect a plurality of parameters associated with the computer-controlled metric appliance 102-1 . . . 102-N and determine the computer-executable goals to be achieved by the computer-controlled metric appliance 102-1 . . . 102-N. The machine learning based task controller 308 may be configured to apply a machine learning model on the plurality of parameters and the computer-executable goal to determine a computer-executable task list to be assigned to the candidate computer-controlled metric appliance 102-1 . . . 102-N in order to achieve the computer-executable goals. The computer-executable task list is assigned to the computer-controlled metric appliance 102-1 . . . 102-N to efficiently allocate goal-based tasks to the computer-controlled metric appliance 102-1 . . . 102-N and to reduce a probability of failures.

If the machine learning based task controller 308 observes medical device failures through collected matrices, the machine learning based task controller 308 automatically generates the task list for regulators to review and assign to the medical device in order to reduce or correct the failures. The details associated with training of the machine learning model are described in conjunction with FIG. 4.

The machine learning based task controller 308 may help to generate the task list by considering various real-time parameters. For example, when a hospital sees many measures and metrics showing patient safety problems, the machine learning based task controller 308 may be used to effectively create a task list and assign the task list to safety staff.

Examples of the parameters include, but is not limited to, a location of the computer-controlled metric appliance 102-1 . . . 102-N, a type of the computer-controlled metric appliance 102-1 . . . 102-N, a capability of the computer-controlled metric appliance 102-1 . . . 102-N, a user associated with the computer-controlled metric appliance 102-1 . . . 102-N, and historic actual values of computer-executable metrics associated with the computer-controlled metric appliance 102-1 . . . 102-N. The machine learning based task controller 308 may utilize one or more of these parameters to assign one or more of the task lists to the computer-controlled metric appliance 102-1 . . . 102-N in view of the goals so that a task list is not just executed as a task but is assigned and executed as a goal-based task-list to achieve certain desired computer-executable goals that may be decided utilizing the one or more parameters. In an example, the task list can be assigned to the computer-controlled metric appliance 102-1 . . . 102-N whenever the computer-controlled metric appliance 102-1 . . . 102-N is in a particular location so that the goal is tied to the location. In an example, the task list can be assigned to the computer-controlled metric appliance 102-1 . . . 102-N whenever the computer-controlled metric appliance 102-1 . . . 102-N is attached to a particular patient or a particular device. In an example, the task list can be assigned to the computer-controlled metric appliance 102-1 . . . 102-N so as to be executed at a particular time. In an example, the task list can be assigned to the computer-controlled metric appliance 102-1 . . . 102-N so as the task list to be executed by the computer-controlled metric appliance 102-1 . . . 102-N whenever a particular event occurs. Similarly, there could be many other goals and parameters to control assigning and execution of the task list without limitations.

FIG. 4, with reference to FIGS. 1 through 3, illustrates a working operation of the machine learning system 110, according to embodiments as disclosed herein. In an embodiment, the machine learning system 110 includes hardware components that are implemented through an AI model 401 to determine the computer-executable task list (Comp. Exe. Task 1 . . . N) to be assigned to the computer-controlled metric appliance 102-1 . . . 102-N in order to achieve one or more computer-executable goals. The hardware components includes special circuitry such as Tensor Processing Unit (TPU), Field Programmable Gate Array (FPGA), logic gates, integrated circuits, microprocessors, microcontrollers, memory circuits, passive electronic components, active electronic components, optical components, hardwired circuits, or the like, and may optionally be driven by firmware and software. The circuitry may, for example, be embodied in one or more semiconductor chips, or on substrate supports such as printed circuit boards and the like.

A function associated with the AI model 401 can be performed through a non-volatile memory (not shown), a volatile memory (not shown), and a processor (not shown). The processor may include one or more processing units. The processor may be a general purpose processor, such as a central processing unit (CPU), an application processor (AP), or the like, a graphics-only processing unit such as a graphics processing unit (GPU), a visual processing unit (VPU), and/or an AI-dedicated processor such as a neural processing unit (NPU).

The processor (not shown in FIG. 4) may control processing of the input data in accordance with a predefined operating rule or the AI model 401 stored in the non-volatile memory and the volatile memory. The predefined operating rule or the artificial intelligence model (AI model) 401 may be provided through training or learning.

The AI model 401 may be trained using various set of parameters, metrics measured by the different types of devices and the one or more goals to be achieved. The various parameters can include, for example, a location of the computer-controlled metric appliance 102-1 . . . 102-N, a type of the computer-controlled metric appliance 102-1 . . . 102-N, a capability of the computer-controlled metric appliance 102-1 . . . 102-N, a user associated with the computer-controlled metric appliance 102-1 . . . 102-N, and historic actual values of the computer-executable metrics associated with the computer-controlled metric appliance 102-1 . . . 102-N.

The AI model 401 may include neural network layers 402 as shown in the FIG. 4. Each layer 402 has a plurality of nodes 403. A value for each of the nodes 403 may be determined based on the parameters, metrics measured by the appliances 102-1 . . . 102-N, and the one or more goals. Each layer 402 performs a layer operation through calculation of a previous layer and an operation on a plurality of weights of the nodes 403.

This learning process may train the AI model 401 using a plurality of learning datasets to cause, allow, or control the machine learning system 110 to make a determination output or prediction output as a set of tasks to be assigned to the computer-controlled metric appliance 102-1 . . . 102-N in order to achieve the one or more computer-executable goals. Examples of such learning techniques include, but are not limited to, supervised learning, unsupervised learning, semi-supervised learning, or reinforcement learning.

For example, if a person is trying to setup a smart club that includes sports, gaming, swimming, and social activities, and cultural activities that requires various kinds of equipment and interaction among different people, then the one or more embodiments discussed herein may be used to automatically create and assign machine learning-based task lists to achieve certain goals. The task lists may be assigned such that respective allocated tasks within the task lists are specific to their respective goals.

The machine learning system 110 may be configured to determine whether the computer-executable metric is achieved or not by comparing the computer-executable metric actually recorded by the computer-controlled metric appliance 102-1 . . . 102-N with the predefined programmable instructions provided to the computer-controlled metric appliance 102-1 . . . 102-N when the goal-based work-list is created and assigned to the computer-controlled metric appliances 102-1 . . . 102-N.

Figure 5A:
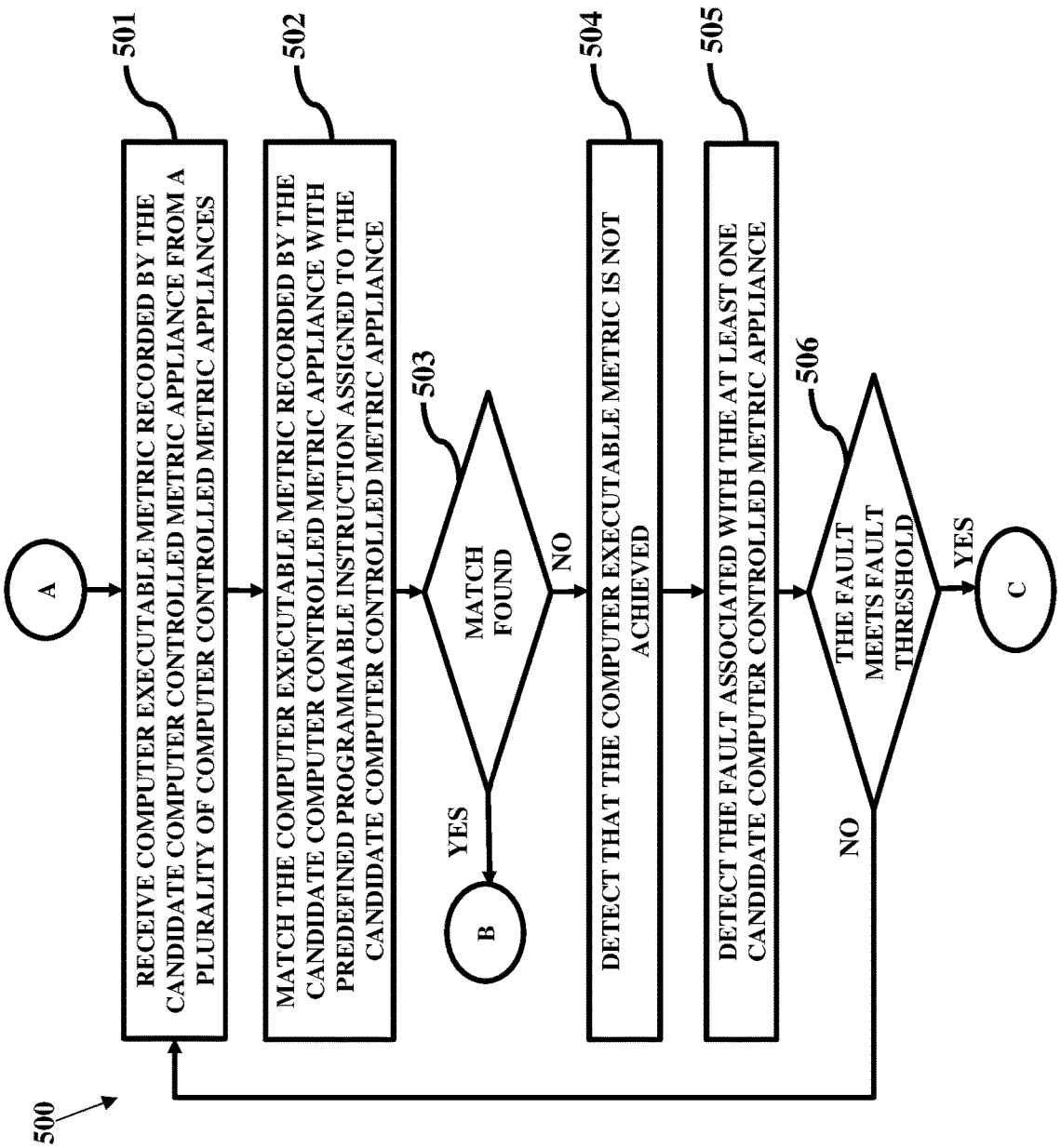

FIGS. 5A-5C, with reference to FIGS. 1 through 4, illustrates a method 500 implemented by the electronic evaluation device 104 for optimizing an operation of the computer-controlled metric appliances 102-1 . . . 102-N.

At step 501, the method 500 includes receiving a computer-executable metric recorded by the computer-controlled metric appliance 102-1 . . . 102-N. Each of the computer-controlled metric appliances 102-1 . . . 102-N records their metrics based on performance delivered by them and send this information to the electronic evaluation device 104 to verify if their respective metrics are achieved or not on a regular basis for performance monitoring and fault detection and also to determine through a second level attestation such as a human attestation whether a fault, if any, is really a fault or something else in case a metric is identified as not achieved.

At step 502, the method 500 includes comparing the computer-executable metric recorded by the computer-controlled metric appliance 102-1 . . . 102-N with the predefined programmable instructions assigned to the computer-controlled metric appliance 102-1 . . . 102-N. The predefined programmable instructions are used to determine whether the computer-executable metric is achieved or not. In order to determine whether the computer-executable metric is achieved or not, a comparison is performed between the computer-executable metric recorded by the computer-controlled metric appliance 102-1 . . . 102-N and the predefined programmable instructions assigned to the computer-controlled metric appliance 102-1 . . . 102-N.

At step 503, the method 500 includes determining whether the comparison results in a performance match indicative of the metric as achieved. In response to determining that the computer-executable metric recorded by the computer-controlled metric appliance 102-1 . . . 102-N does not match with the predefined programmable instructions assigned to the computer-controlled metric appliance 102-1 . . . 102-N, at step 504, the method 500 may include generating a signal indicating that the computer-executable metric is not achieved. Upon detecting the computer-executable metric as not achieved, at step 505, the method 500 includes detecting a fault associated with the computer-controlled metric appliance 102-1 . . . 102-N. The computer-executable metric is said to be not achieved and a fault is declared with the computer-controlled metric appliance 102-1 . . . 102-N if the match is not established after the comparison.

With a detection of the fault, at step 506, the method 500 includes determining whether the fault associated with the computer-controlled metric appliance 102-1 . . . 102-N crosses a fault threshold. In response to determining that the fault associated with the computer-controlled metric appliance 102-1 . . . 102-N crosses the fault threshold, at step 507, the method 500 includes reporting the fault associated with the computer-controlled metric appliance to the validation entity 108. In an embodiment, the reporting of the fault is performed by sending a message to the validation entity 108.

At step 508, the method 500 includes receiving the feedback about the fault in real time from the validation entity 108 and at step 509, the method 500 includes determining whether the fault is valid based on the real time feedback received from the validation entity 108 or not.

In response to determining that the fault is valid, at step 510, the method 500 includes automatically updating the predefined programmable instructions assigned to the candidate computer-controlled metric appliance based on the feedback.

In an example without limitations, at step 511, the method 500 may include detecting a plurality of parameters associated with the computer-controlled metric appliance 102-1 . . . 102-N. The plurality of parameters may include a location of the computer-controlled metric appliance 102-1 . . . 102-N, a type of the computer-controlled metric appliance 102-1 . . . 102-N, a capability of the computer-controlled metric appliance 102-1 . . . 102-N, a user associated with the computer-controlled metric appliance 102-1 . . . 102-N, and historic actual values of the computer-executable metrics of the computer-controlled metric appliance 102-1 . . . 102-N.

At step 512, the method 500 may include determining one or more computer-executable goals to be achieved by the computer-controlled metric appliance 102-1 . . . 102-N. At step 513, the method 500 may include applying one or more machine learning models on the plurality of parameters and the one or more computer-executable goals to determine a set of computer-executable tasks to be assigned to the computer-controlled metric appliance 102-1 . . . 102-N in order to achieve the one or more computer-executable goals through the task lists.

At step 514, the method 500 may include assigning the computer-executable task lists to the computer-controlled metric appliance 102-1 . . . 102-N.

At step 515, the method 500 may include updating the machine learning model in response to detecting that the computer-executable metric is achieved or not. The computer-executable metric is determined to be achieved or not by comparing the computer-executable metric recorded by the computer-controlled metric appliance 102-1 . . . 102-N with the predefined programmable instructions assigned to the computer-controlled metric appliance 102-1 . . . 102-N. The computer-executable metric is considered as not achieved in response to determining that the computer-executable metric recorded by the computer-controlled metric appliance does not match with the pre-defined programmable instructions assigned to the computer-controlled metric appliance 102-1 . . . 102-N. The machine learning models may be corrected to optimize assigning and/or prediction of the task lists for the computer-controlled metric appliance 102-1 . . . 102-N.

In an example, the method 500 may include generating an output signal by the electronic evaluation device 104, wherein the output signal triggers a change in operation of the computer-controlled metric appliance such as the computer-controlled metric appliance 101-1 if the fault is identified to be valid. In an example, the change in operation of the computer-controlled metric appliance 101-1 may include executing one or more tasks by the computer-controlled metric appliance 101-1 in accordance with an updated set of the predefined programmable instructions after the feedback.

The various actions, acts, blocks, steps, or the like in the flowcharts of FIGS. 5A-5C may be performed in the order presented, in a different order or simultaneously. Further, in some embodiments, some of the actions, acts, blocks, steps, or the like can be omitted, added, modified, skipped, or the like without departing from the scope of the invention.

It will be understood that each acts, blocks, steps, or the like in the flowcharts of FIGS. 5A-5C can be implemented by computer program instructions using special purpose hardware-based computer systems which perform the specified functions or steps, or combinations of special purpose hardware and computer instructions. These computer program instructions may be loaded onto a computer or other programmable apparatus to produce a machine, such that the instructions which execute on the computer or other programmable apparatus create means for implementing the functions specified in the block diagram, flowchart or control flow block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the function specified in the flowchart. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions specified in the block diagram, flowchart or control flow block(s) or step(s).

In an embodiment, the worklist management system 112 may be utilized for evidence-based engineering also referred to as 'evidence engineering' in an exemplary embodiment. The processor 302 of the worklist management system 112 may be configured to define target outcomes and objectives in a machine-readable format referred to as computer-executable 'evidence targets' for a workflow or a set of task. The processor 302 may be configured to define a plurality of 'evidence signals' and associate each of the evidence signals with a respective evidence target. The evidence signals are indicative of defined measurable key results for evaluating performance of the computer-controlled medical appliances 102-1 . . . 102-N in the network 106 such that values of the evidence signals may be gathered by collecting metrics in the network 106. Each metric collected from a computer-controlled metric appliance such as the metric appliance 102-1 . . . 102-N for a specific task or a series of tasks as governed through a worklist executed by the worklist management system 112 may represent an evidence signal that may be compared with a corresponding measurable key result to identify the extent to which the evidence signal as achieved the evidence target. Any evidence signal irrespective of whether the computer-controlled metric appliance 102-1 . . . 102-N achieves or does not achieve the evidence target is suitable to be considered as an evidence-based input for various tasks performed in the network. Metadata may be associated with each such evidence-based input to recognize and read the impact of the evidence signal for achieving the respective evidence target when a series of specific tasks is performed so that futuristic models may determine optimal and efficient solutions for worklist execution not based on pure assumptions but based on evidences collected from past metrics in the form of evidence signals. Each evidence signal represents an evidence-based input for a user or a machine to evaluate, employ, and make machine-based decisions accordingly for executing various tasks irrespective of whether the evidence-based input delivered weak performance or strong performance in past as long as the evidence-based inputs (evidence signals) are well defined, collected, and stored for decision making.

The worklist management system 112 may establish data engineering processes and tools necessary to continuously collect and process data (the process referred to as 'evidentiary data collection') to help understand if the key results are met against the defined evidence targets by measuring the evidence signals. This may be achieved by regularly collecting the metrics associated with the computer-controlled metric appliances 102-1 . . . 102-N in the network 106.

An evidence engineering-based worklist execution or operation model referred to as EvidenceOps herein and as executed by the worklist management system 112 gathers the data or the metrics or the evidence signals, compares them against evidence targets and then makes decisions about how to autonomously, automatically, or with limited minimal human intervention adjusts behavior of a system or the computer-controlled metric appliance 102-1 . . . 102-N etc. given the evidence recorded within the network 106.

Evidence or EvidenceOps is utilized in engineering or modeling process because it gives credibility to the findings, recommendations, and decision making. Machine readable evidence is reliable information that support and justify analytical processes, findings and the recommendations. The system 100 disclosed herein may be deployed in command centers, wherein the system 100 can take aggregated metrics and data that is coming various devices in an operation environment. The system 100 may get metrics from ten different data centers, for example, and be able to use trusted networks. The system 100 may utilize automated rules so that operational monitoring can be performed. An alert may be generated in case of errors in operations which may become defined as "an incident" so that instead of just starting and reporting the incident as an event or error, the system can tie that to a predefined incident response such as in the form of a task list or a worklist including one or a series of tasks for executing corrective measures.

The system 100 allows aggregation of the metrics from several devices and also matching of a rule. The system 100 also ensures that an action or a response is taken to rectify a particular need or meet a goal and those actions are then recorded somewhere in a database. The response is then tied back to the original set of metrics to teach a device whether or not this was the right step of action that should have been performed in the first place. If a response is found to be incorrect, the system 100 provides a predefined set of rules along with predefined set of incident responses that trigger the incident response based on the rules that will retreat from the metrics and then let the devices or humans do their work and then roll that back into the system 100.

The system 100 allows aggregation of the metrics across the network 106 and maintain them in the network (such as in a blockchain network or in any other trusted network) and allows some actions that need to be taken as responses in view of certain incidences that may occur in different locations such as data centers and different hospitals or other units.

The collecting of metrics and reporting and alerting is followed by actions or tasks that are to be executed.

The system 100 may store in a database commonly considered responses and incidents that can be covered as use-cases and use them as rules for driving the task lists for the devices (or metric appliances).

In an example, for a task list selection for achieving certain goals, the system 100 will define them first and then identify the metrics which were aggregated from the devices to match certain rules and provide an action plan from associated one or two or many more worklists that drive actions of the devices.

In an example, the system 100 may utilize open policy agency, CUE (scoring DSL), and related evaluation techniques for metrics across multiple ecosystems (for example, checking one metric in a human-attestation against a real metric coming out of a hardware device to validate data).

In an example, the embodiments herein can provide a computer program product configured to include a pre-configured set of instructions, which when performed, can result in actions as stated in conjunction with various figures herein. In an example, the pre-configured set of instructions can be stored on a tangible non-transitory computer readable medium. In an example, the tangible non-transitory computer readable medium can be configured to include the set of instructions, which when performed by a device, can cause the device to perform acts similar to the ones described here.

The embodiments herein may also include tangible and/or non-transitory computer-readable storage media for carrying or having computer-executable instructions or data structures stored thereon. Such non-transitory computer readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a special purpose computer or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network. If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

The invention described herein improvises overall hardware performance of the computer-controlled metric appliances 102 as the predefined programmable instructions defined for the computer-controlled metric appliances 102 are automatically updated as needed to change an expected outcome of the computer-executable metric based on actual requirements instead of delivering faulty or inaccurate performance by the computer-controlled metric appliances 102.

The computer-controlled metric appliances 102 hence will better be able to operate to achieve the metric based on updated predefined programmable instructions after the evaluation. This enables efficient use of the computer-controlled metric appliances 102. With the updated predefined programmable instructions, the operation of the computer-controlled metric appliance will automatically change so as to deliver the expected performance which results in optimization.

Figure 6:
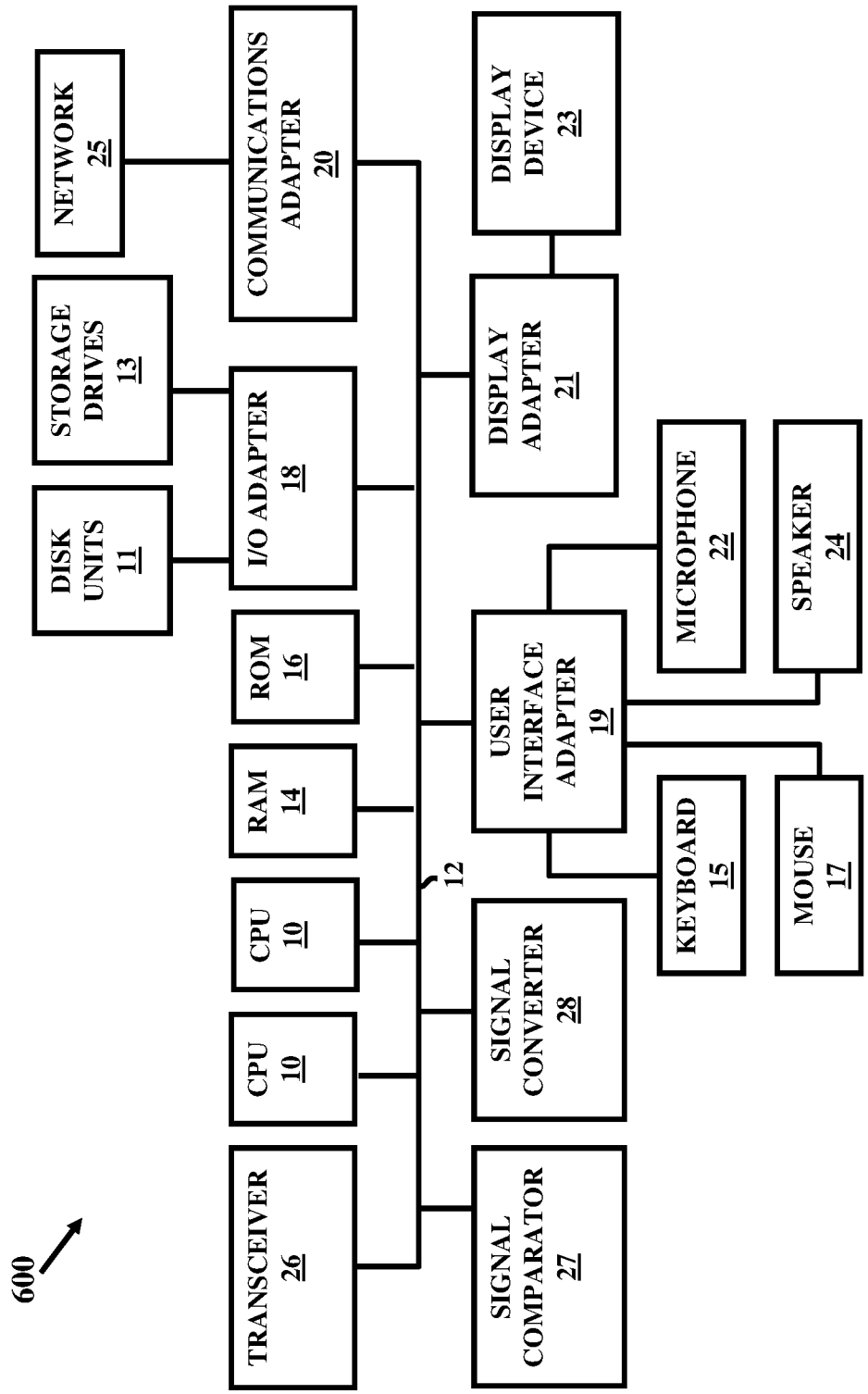
FIG. 6 is a block diagram illustrating a computer system according to an embodiment herein.

A representative hardware environment for practicing the embodiments herein is depicted in FIG. 6, with reference to FIGS. 1 through 5C. This schematic drawing illustrates a hardware configuration of an information handling/computer system 600 in accordance with the embodiments herein. The system 600 comprises at least one processor or central processing unit (CPU) 10. The CPUs 10 are interconnected via system bus 12 to various devices such as a random-access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system 600. The system 600 can read the inventive instructions on the program storage devices and follow these instructions to execute the methodology of the embodiments herein. The system 600 further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network, and a display adapter 21 connects the bus 12 to a display device 23 which may be embodied as an output device such as a monitor, printer, or transmitter, for example. Further, a transceiver 26, a signal comparator 27, and a signal converter 28 may be connected with the bus 12 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A computer-implemented method for optimizing an operation of computer-controlled metric appliances in a network, the method comprising:

receiving, by an electronic evaluation device, a computer-executable metric recorded by a computer-controlled metric appliance from the computer-controlled metric appliances;

detecting, by the electronic evaluation device, a fault associated with the computer-controlled metric appliance based on predefined programmable instructions provided to the computer-controlled metric appliance, wherein the predefined programmable instructions are used to determine whether the computer-executable metric is achieved or not;

receiving, by the electronic evaluation device, a feedback about the fault in real time from a validation entity in response to detecting the fault;

determining, by the electronic evaluation device, whether the fault associated with the computer-controlled metric appliance is valid based on the feedback received in real time from the validation entity;

automatically updating, by the electronic evaluation device, the predefined programmable instructions provided to the computer-controlled metric appliance based on the feedback in response to determining that the fault is invalid, such that the predefined programmable instructions, after updating, changes an expected outcome of the computer-executable metric resulting in an optimized performance of the computer-controlled metric appliance; and generating an output signal by the electronic evaluation device, wherein the output signal triggers a change in operation of the computer-controlled metric appliance when the fault is identified to be valid, and wherein the change in operation of the computer-controlled metric appliance signifies executing one or more tasks by the computer-controlled metric appliance based on an updated set of the predefined programmable instructions.

2. The method of claim 1, wherein detecting, by the electronic evaluation device, the fault associated with the computer-controlled metric appliance based on the predefined programmable instructions comprises:

determining, by the electronic evaluation device, whether the computer-executable metric is achieved or not by comparing the computer-executable metric recorded by the computer-controlled metric appliance with the predefined programmable instructions provided to the computer-controlled metric appliance;

detecting, by the electronic evaluation device, that the computer-executable metric is not achieved in response to determining that the computer-executable metric recorded by the computer-controlled metric appliance does not match with the predefined programmable instructions provided to the computer-controlled metric appliance; and detecting, by the electronic evaluation device, the fault associated with the computer-controlled metric appliance in response to determining that the computer-executable metric is not achieved.

3. The method of claim 1, wherein receiving, by the electronic evaluation device, the feedback about the fault in real time from the validation entity in response to detecting the fault comprises:

determining, by the electronic evaluation device, whether the fault associated with the computer-controlled metric appliance meets a fault threshold in response to detecting the fault;

reporting, by the electronic evaluation device, the fault associated with the computer-controlled metric appliance to the validation entity in response to determining that the fault associated with the computer-controlled metric appliance meets the fault threshold; and receiving, by the electronic evaluation device, the feedback about the fault in real time from the validation entity.

4. The method of claim 1, wherein the method further comprises:

detecting, by the electronic evaluation device, a plurality of parameters associated with the candidate computer-controlled metric appliance;

determining, by the electronic evaluation device, a computer-executable goal to be achieved by the computer-controlled metric appliance;

applying, by the electronic evaluation device, a machine learning model on the plurality of parameters and the computer-executable goal to determine a computer-executable task to be assigned to the computer-controlled metric appliance to achieve the computer-executable goal; and assigning, by the electronic evaluation device, the computer-executable task to the computer-controlled metric appliance.

5. The method of claim 4, wherein determining, by the electronic evaluation device, the computer-executable goal to be achieved by the computer-controlled metric appliance comprises:

receiving, by the electronic evaluation device, an input from an external entity; and determining, by the electronic evaluation device, the computer-executable goal to be achieved by the candidate computer-controlled metric appliance based on the input.

6. The method of claim 4, wherein the method further comprises:

receiving, by the electronic evaluation device, the computer-executable metric recorded by the computer-controlled metric appliance;

determining, by the electronic evaluation device, whether the computer-executable metric is achieved or not by comparing the computer-executable metric recorded by the computer-controlled metric appliance with the predefined programmable instructions provided to the computer-controlled metric appliance; and performing, by the electronic evaluation device, one of:
detecting that the computer-executable metric is not achieved in response to determining that the computer-executable metric recorded by the computer-controlled metric appliance does not match with the predefined programmable instructions provided to the computer-controlled metric appliance, detecting the fault associated with the computer-controlled metric appliance in response to determining that the computer-executable metric is not achieved, and correcting the machine learning model to optimize determination of the computer-executable task assigned to the computer-controlled metric appliance, and detecting that the computer-executable metric is achieved in response to determining that the computer-executable metric recorded by the computer-controlled metric appliance matches with the predefined programmable instructions provided to the computer-controlled metric appliance, and updating the machine learning model in response to detecting that the computer-executable metric is achieved.

7. The method of claim 4, wherein the plurality of parameters comprises a location of the computer-controlled metric appliance, a type of the computer-controlled metric appliance, a capability of the computer-controlled metric appliance, a user associated with the computer-controlled metric appliance, and historic values of the computer-executable metric generated by the computer-controlled metric appliance.

8. A computer-implemented method for optimizing an operation of computer-controlled metric appliances in a network, comprising:

detecting, by an electronic evaluation device, a plurality of parameters associated with a candidate computer-controlled metric appliance from the computer-controlled metric appliances;

determining, by the electronic evaluation device, a computer-executable goal to be achieved by the candidate computer-controlled metric appliance;

determining, by the electronic evaluation device, a computer-executable task list to be assigned to the candidate computer-controlled metric appliance to achieve the computer-executable goal based on the plurality of parameters and the computer-executable goal by applying a machine learning model;

assigning, by the electronic evaluation device, the computer-executable task list to the candidate computer-controlled metric appliance, wherein the assigning of the computer-executable task list to the candidate computer-controlled metric appliance facilitates achieving the computer-executable goal by the candidate computer-controlled metric appliance;

receiving, by the electronic evaluation device, a computer-executable metric recorded by the candidate computer-controlled metric appliance;

determining, by the electronic evaluation device, whether the computer-executable metric is achieved or not by comparing the computer-executable metric recorded by the candidate computer-controlled metric appliance with the predefined programmable instructions provided to the candidate computer-controlled metric appliance; and performing, by the electronic evaluation device, one of:
  detecting that the computer-executable metric is not achieved in response to determining that the computer-executable metric recorded by the candidate computer-controlled metric appliance does not match with the predefined programmable instructions provided to the candidate computer-controlled metric appliance, detecting the fault associated with the candidate computer-controlled metric appliance in response to determining that the computer-executable metric is not achieved, and correcting the machine learning model to optimize determination of the computer-executable task list to be assigned to the candidate computer-controlled metric appliance, and
  detecting that the computer-executable metric is achieved in response to determining that the computer-executable metric recorded by the candidate computer-controlled metric appliance matches with the predefined programmable instructions provided to the candidate computer-controlled metric appliance, and updating the machine learning model in response to detecting that the computer-executable metric is achieved.

9. The method of claim 8, wherein determining, by the electronic evaluation device, the computer-executable goal to be achieved by the candidate computer-controlled metric appliance comprises:
  receiving, by the electronic evaluation device, an input from an external entity; and
  determining, by the electronic evaluation device, the computer-executable goal to be achieved by the candidate computer-controlled metric appliance based on the input.

10. The method of claim 8, wherein the plurality of parameters comprises a location of the candidate computer-controlled metric appliance, a type of the candidate computer-controlled metric appliance, a capability of the candidate computer-controlled metric appliance, a user associated with the candidate computer-controlled metric appliance, and historic computer-executable metrics of the candidate computer-controlled metric appliance.

11. The method of claim 8, wherein the method further comprising:
  receiving, by the electronic evaluation device, a feedback about the fault in real time from a validation entity in response to detecting the fault;
  determining, by the electronic evaluation device, whether the fault associated with the candidate computer-controlled metric appliance is valid based on the feedback received in real time from the validation entity; and
  automatically updating, by the electronic evaluation device, predefined programmable instructions based on the feedback in response to determining that the fault is invalid.

12. The method of claim 11, wherein receiving, by the electronic evaluation device, the feedback about the fault in real time from the validation entity in response to detecting the fault comprises:
  determining, by the electronic evaluation device, whether the fault associated with the candidate computer-controlled metric appliance meets a fault threshold in response to detecting the fault;
  reporting, by the electronic evaluation device, the fault associated with the candidate computer-controlled metric appliance to the validation entity in response to determining that the fault associated with the candidate computer-controlled metric appliance meets the fault threshold; and
  receiving, by the electronic evaluation device, the feedback about the fault in real time from the validation entity.

13. An electronic evaluation device for optimizing an operation of computer-controlled metric appliances in a network, comprising:
  a memory;
  a processor; and
  a computer-executable metric validation controller, communicatively coupled to the memory and the processor, wherein the computer-executable metric validation controller is to:
    receive a computer-executable metric recorded by a candidate computer-controlled metric appliance from the computer-controlled metric appliances;
    detect a fault associated with the candidate computer-controlled metric appliance based on predefined programmable instructions provided to the candidate computer-controlled metric appliance, wherein the predefined programmable instructions are used to determine whether the computer-executable metric is achieved or not;
    receive a feedback about the fault in real time from a validation entity in response to detecting the fault;
    determine whether the fault associated with the candidate computer-controlled metric appliance is valid based on the feedback received in real time from the validation entity; and
    automatically update the predefined programmable instructions based on the feedback in response to determining that the fault is invalid, wherein an updating of the predefined programmable instructions allows the candidate computer-controlled metric appliance to achieve the computer-executable metric;

determine whether the fault associated with the candidate computer-controlled metric appliance meets a fault threshold in response to detecting the fault;

report the fault associated with the candidate computer-controlled metric appliance to the validation entity in response to determining that the fault associated with the candidate computer-controlled metric appliance meets the fault threshold; and receive the feedback about the fault in real time from the validation entity.

14. The electronic evaluation device of claim 13, further configured to:

determine whether the computer-executable metric is achieved or not by comparing the computer-executable metric recorded by the candidate computer-controlled metric appliance with the predefined programmable instructions provided to the candidate computer-controlled metric appliance;

detect that the computer-executable metric is not achieved in response to determining that the computer-executable metric recorded by the candidate computer-controlled metric appliance does not match the predefined programmable instructions assigned to the candidate computer-controlled metric appliance; and detect the fault associated with the candidate computer-controlled metric appliance in response to determining that the computer-executable metric is not achieved.

15. The electronic evaluation device of claim 13, wherein the electronic evaluation device comprising a machine learning based task controller configured to:

detect a plurality of parameters associated with the candidate computer-controlled metric appliance;

determine a computer-executable goal to be achieved by the candidate computer-controlled metric appliance;

apply a machine learning model on the plurality of parameters and the computer-executable goal to determine a computer-executable task to be assigned to the candidate computer-controlled metric appliance to achieve the computer-executable goal; and assign the computer-executable task to the candidate computer-controlled metric appliance.

16. The electronic evaluation device of claim 15, further configured to:

receive an input from an external entity; and determine the computer-executable goal to be achieved by the candidate computer-controlled metric appliance based on the input.

17. The electronic evaluation device of claim 15, wherein the machine learning based task controller is configured to:

receive a computer-executable metric recorded by a candidate computer-controlled metric appliance;

determine whether the computer-executable metric is achieved or not by comparing the computer-executable metric recorded by the candidate computer-controlled metric appliance with the predefined programmable instructions provided to the candidate computer-controlled metric appliance; and perform one of:

detecting that the computer-executable metric is not achieved in response to determining that the computer-executable metric recorded by the candidate computer-controlled metric appliance does not match with the predefined programmable instructions assigned to the candidate computer-controlled metric appliance, detecting the fault associated with the candidate computer-controlled metric appliance in response to determining that the computer-executable metric is not achieved, and correcting the machine learning model to optimize determination of the computer-executable task to be assigned to the candidate computer-controlled metric appliance; and detecting that the computer-executable metric is achieved in response to determining that the computer-executable metric recorded by the candidate computer-controlled metric appliance matches with the predefined programmable instructions assigned to the candidate computer-controlled metric appliance, and updating the machine learning model in response detecting that the computer-executable metric is achieved.

18. The electronic evaluation device of claim 15, wherein the plurality of parameters comprises a location of the candidate computer-controlled metric appliance, a type of the candidate computer-controlled metric appliance, a capability of the candidate computer-controlled metric appliance, a user associated with the candidate computer-controlled metric appliance, and a historic value of the computer-executable metric associated with the candidate computer-controlled metric appliance.

19. An electronic evaluation device for optimizing an operation of computer-controlled metric appliances in a network, comprising:

a memory;

a processor;

a computer-executable metric validation controller, communicatively coupled to the memory and the processor, wherein the computer-executable metric validation controller is configured to:

detect a plurality of parameters associated with a candidate computer-controlled metric appliance from the computer-controlled metric appliances;

determine a computer-executable goal to be achieved by the candidate computer-controlled metric appliance;

determine a computer-executable task list to be assigned to the candidate computer-controlled metric appliance to achieve the computer-executable goal based on the plurality of parameters and the computer-executable goal by applying a machine learning model; and assign the computer-executable task list to the candidate computer-controlled metric appliance, wherein an assigning of the computer-executable task list to the candidate computer-controlled metric appliance facilitates achieving the computer-executable goal by the candidate computer-controlled metric appliance;

a machine learning based task controller configured to:

receive a computer-executable metric recorded by a candidate computer-controlled metric appliance;

determine whether the computer-executable metric is achieved or not by matching the computer-executable metric recorded by the candidate computer-controlled metric appliance with the predefined programmable instructions assigned to the candidate computer-controlled metric appliance; and perform one of:

detecting that the computer-executable metric is not achieved in response to determining that the computer-executable metric recorded by the candidate computer-controlled metric appliance does not matches with the predefined programmable instructions assigned to the candidate computer-controlled metric appliance, detect the fault associated with the candidate computer-controlled metric appliance in response to determining that the computer-executable metric is not achieved, and correct the machine learning model to optimize determination of the computer-executable task to be assigned to the candidate computer-controlled metric appliance; and detecting that the computer-executable metric is achieved in response to determining that the computer-executable metric recorded by the candidate computer-controlled metric appliance matches with the predefined programmable instructions assigned to the candidate computer-controlled metric appliance, and update the machine learning model in response detecting that the computer-executable metric is achieved.

20. The electronic evaluation device of claim 19, further configured to:

receive an input from an external entity; and determine the computer-executable goal to be achieved by the candidate computer-controlled metric appliance based on the input.

21. The electronic evaluation device of claim 19, wherein the plurality of parameters comprises a location of the candidate computer-controlled metric appliance, a type of the candidate computer-controlled metric appliance, a capability of the candidate computer-controlled metric appliance, a user associated with the candidate computer-controlled metric appliance, and a historic computer-executable metrics of the candidate computer-controlled metric appliance.

22. The electronic evaluation device of claim 19, wherein the machine learning based task controller is configured to:

receive a feedback about the fault in real time from a validation entity in response to detecting the fault;

determine whether the fault associated with the candidate computer-controlled metric appliance is valid based on the feedback received in real time from the validation entity; and automatically update predefined programmable instructions based on the feedback in response to determining that the fault is invalid.

23. The electronic evaluation device of claim 22, wherein receiving the feedback about the fault in real time from the validation entity in response to detecting the fault comprises:

determining whether the fault associated with the candidate computer-controlled metric appliance meets a fault threshold in response to detecting the fault;

reporting the fault associated with the candidate computer-controlled metric appliance to the validation entity in response to determining that the fault associated with the candidate computer-controlled metric appliance meets the fault threshold; and receiving the feedback about the fault in real time from the validation entity.

24. A computer-implemented method for optimizing an operation of computer-controlled metric appliances in a network, the method comprising:

receiving, by an electronic evaluation device, a computer-executable metric recorded by a computer-controlled metric appliance from among the computer-controlled metric appliances, wherein the computer-executable metric is generated based on predefined programmable instructions for the computer-controlled metric appliance;

detecting, by the electronic evaluation device, a set of data inputs requiring a refinement in the predefined programmable instructions provided to the computer-controlled metric appliance, wherein the predefined programmable instructions are used to determine whether the computer-executable metric is achieved or not based on assigned computer-executable tasks; and automatically updating, by the electronic evaluation device, the predefined programmable instructions provided to the computer-controlled metric appliance such that the pre-defined programmable instructions after updating changes an expected outcome of the computer-executable metric resulting in an optimized performance of the computer-controlled metric appliance; and generating an output signal by the electronic evaluation device, wherein the output signal triggers a change in operation of the computer-controlled metric appliance when the fault is identified to be valid, and wherein the change in operation of the computer-controlled metric appliance signifies executing one or more tasks by the computer-controlled metric appliance based on an updated set of the predefined programmable instructions.

* * * * *